United States Patent [19]

Mori et al.

[11] Patent Number: 5,292,415
[45] Date of Patent: Mar. 8, 1994

[54] CHLORO-TERMINATED POLYSILANE AND PROCESS FOR MAKING

[75] Inventors: Shigeru Mori; Eiichi Tabei; Hisashi Umehara, all of Kawasaki, Japan

[73] Assignee: Shin-Etsu Chemical Company, Limited, Tokyo, Japan

[21] Appl. No.: 6,487

[22] Filed: Jan. 21, 1993

[30] Foreign Application Priority Data

Jan. 21, 1992 [JP] Japan .................................. 4-30103
Mar. 27, 1992 [JP] Japan .................................. 4-101804

[51] Int. Cl.$^5$ ............................. C07F 7/08; C07B 9/00
[52] U.S. Cl. ......................... 204/157.64; 204/157.74; 556/430; 528/25
[58] Field of Search ................... 556/430; 204/157.64; 528/25

[56] References Cited

U.S. PATENT DOCUMENTS

4,716,240  12/1987  Nagal et al. ....................... 556/430

FOREIGN PATENT DOCUMENTS

234412   9/1987  European Pat. Off. ........... 556/430
61-238790 10/1986  Japan ................................. 556/430

OTHER PUBLICATIONS

Gilman et al., *J. Organomet. Chem.*, 8, (1967), pp. 451–457.

Zhang, et al. (1984) Journal of Polymer Science:-Polymer Chem. Edition 22:159–170.
R. West, (1986) Journal of Organometallic Chemistry 300:327–346.
Kagaku to Kogyo (Chemistry & Industry, vol. 42, No. 4, pp. 744–747 (Feb. 3, 1970).
Kumada, et al., (1964) Journal of Organometallic Chemistry, 2:478–484.
Ishikawa, et al. (1970) Journal of Organometallic Chemistry 23:63–69.
Wolff, et al., (1987) Applied Organometallic Chemistry 1:7–14.

*Primary Examiner*—Paul F. Shaver
*Attorney, Agent, or Firm*—Birch, Stewart, Kolasch & Birch

[57] ABSTRACT

The invention provides a novel chloro-terminated polysilane of the formula:

$$Cl[(R^1R^2Si)_n (R^3R^4Si)_m]_k Cl \qquad (1)$$

wherein $R^1$, $R^2$, $R^3$ and $R^4$ are alkyl and aryl groups, n, m and k are numbers in the range: $0 \leq n \leq 10$, $0 \leq m \leq 10$, $n+m \geq 10$, and $k \geq 1$, especially $k \geq 5$. It is prepared by exposing a high-molecular weight polysilane in chlorinated hydrocarbon to ultraviolet radiation in an inert gas atmosphere.

10 Claims, No Drawings

CHLORO-TERMINATED POLYSILANE AND PROCESS FOR MAKING

BACKGROUND OF THE INVENTION

1. Field of the Invention

This invention relates to a α,ω-chloro terminated polysilane capable of accepting any desired functional group and useful as a source material for forming copolymers with other polymers as well as a process for preparing the same.

2. Prior Art

Most industrial processes for preparing polysilanes utilize coupling reaction of dihalogenosilanes with alkali metals as reported in Journal of Polymer Science: Polymer Chemistry Edition, Vol. 22, 159–170 (1984) and Journal of Organometallic Chemistry, Vol. 300, 327 (1986). These processes produce polysilanes in the form of mixtures of cyclic polymers and halo—or hydrogen-terminated polymers. It is difficult to quantitatively obtain terminally modified polymers from these mixtures.

With respect to the synthesis of single end modified polysilanes, Sakurai et al. attempted living polymerization from polymers containing a disilane unit for introducing hydrogen or carboxylic acid as well as copolymerization of such polymers with polymethyl methacrylate (PMMA) as reported in Kagaku to Kogyo (Chemistry & Industry), Vol. 42, No. 4, 744. This attempt, however, has several industrial problems including limited type of substituents and limited availability of monomers.

Exemplary synthesis of both and single end reactive polysilanes is reported in Journal of Organometallic Chemistry, Vol. 2, 478–484 (1964) and Journal of Organometallic Chemistry, Vol. 23, 63–69 (1970). More specifically, chloro-terminated oligosilanes can be prepared by reacting permethyloligosilanes with acetyl chloride in the presence of aluminum chloride. Also chloro-terminated oligosilanes can be prepared by reacting phenyl-terminated oligo-silanes with hydrogen chloride or chlorosilane in the presence of aluminum chloride. These chloro-terminated oligosilanes, however, have a low degree of polymerization.

SUMMARY OF THE INVENTION

Therefore, an object of the present invention is to provide a novel and improved chloro-terminated polysilane with a high degree of polymerization capable of accepting any desired functional group and suitable as a source material for forming copolymers with other polymers. Another object is to provide a process for preparing such a chloro-terminated polysilane.

Focusing on the reaction that on exposure to ultraviolet (UV) radiation, polysilanes decompose and convert to those of a lower molecular weight while yielding highly reactive silylene and silyl radicals as reported in Applied Organometallic Chemistry, Vol. 1, 7–14 (1987), the inventors have found that when high-molecular weight polysilanes are photo-decomposed by selecting a chlorinated hydrocarbon as a solvent prone to chlorine withdrawal and exposing the polysilanes to UV radiation in the chlorinated hydrocarbon, silyl radicals generate and then form chloro-terminated polysilanes having a high degree of polymerization.

More specifically, coupling reaction of dichlorosilane with alkali metal yields a high-molecular weight polysilane which is a mixture of a cyclic polymer and a halo—or hydrogen-terminated polymer as previously mentioned. When such a polysilane is exposed to UV radiation, the cyclic polymer opens its ring and converts into a chloro-terminated polysilane through photo-decomposition. At the same time, the halo—or hydrogen-terminated polymer remains unreactive where it has a terminal halogen atom, but where it has a terminal hydrogen atom, the hydrogen atom is replaced by a chlorine atom under the action of light or heat. As a result, from high-molecular weight polysilane, there is obtained a chloro-terminated polysilane having a lower molecular weight which is dictated by the dose of UV radiation.

Accordingly, the present invention provides a both end chloro-terminated polysilane of the formula:

Cl[(R¹R²Si)n (R³R⁴Si)m]kCl     (1)

wherein $R^1$, $R^2$, $R^3$ and $R^4$ are independently monovalent hydrocarbon groups having 1 to 12 carbon atoms selected from substituted or unsubstituted alkyl and aryl groups, letters n, m and k are numbers in the range: $0 \leq n \leq 10$, $0 \leq m \leq 10$, $n+m \geq 10$, and $k \geq 1$.

In a second aspect, the present invention provides a process for preparing a chloro-terminated polysilane. A solution of a high-molecular weight polysilane in a chlorinated hydrocarbon is exposed to UV radiation in an inert gas atmosphere, thereby forming a both end chloro-terminated polysilane.

DETAILED DESCRIPTION OF THE INVENTION

The chloro-terminated polysilane of the present invention is represented by formula (1).

Cl[R¹R²Si)n (R³R⁴Si)m]kCl     (1)

In formula (1), $R^1$, $R^2$, $R^3$ and $R^4$, which may be identical or different, are monovalent hydrocarbon groups having 1 to 12 carbon atoms, preferably 1 to 10 carbon atoms selected from substituted or unsubstituted alkyl and aryl groups. The alkyl groups include methyl, ethyl and propyl groups and the aryl groups include phenyl and tolyl groups. Letters n, m and k are numbers in the range: $0 \leq n \leq 10$, $0 \leq m \leq 10$, $n+m \geq 10$, and $k \geq 1$. Preferably, k is 5 or more, especially 10 or more, in order that the polysilane exert photoconductivity and other desired properties. The term chloro-terminated means that the polysilane is terminated with chlorine at both ends of its molecular chain unless otherwise stated.

The chloro-terminated polysilane of formula (1) is prepared by first effecting coupling reaction of a dichlorosilane with an alkali metal such as sodium for forming a polysilane. The dichlorosilane used herein should preclude the use of dimethyldichlorosilane alone. Aromatic group-containing dichlorosilanes such as methylphenyldichlorosilane and ethylphenyldichlorosilane, dichlorosilanes having a $C_2$ or higher aliphatic group such as methylethyldichlorosilane, methylpropyldichlorosilane, methylhexyldichlorosilane and dihexyldichlorosilane may be used alone or in admixture of two or more. The coupling reaction results in a polysilane of the general formula (2):

(R¹R²Si)n'(R³R⁴Si)m'     (2)

wherein $R^1$, $R^2$, $R^3$ and $R^4$ are as defined above, $0 \leq n'$, $0 \leq m'$, $10 \leq n'+m'$, preferably $30 \leq n'+m'$. It preferably has a number average molecular weight (Mn) of 1,000 to 1,000,000, more preferably 5,000 to 1,000,000.

Next, the polysilane is dissolved in a chlorinated hydrocarbon solvent and exposed to UV radiation in an inert gas atmosphere. Examples of the chlorinated hydrocarbon used herein include dichloromethane, chloroform, carbon tetrachloride, 1,2-dichloroethane, 1,1,2-trichloroethane, and 1,1,2,2-tetrachloroethane alone or in admixture of two or more.

Preferably, the polysilane is dissolved in a chlorinated hydrocarbon to form a solution at a concentration of about 1 to 20% by weight, more preferably about 1 to 10% by weight. The polysilane solution is sealingly filled in a Pyrex® or quartz reaction tube and irradiated with UV radiation in an inert gas atmosphere using a high pressure mercury lamp (312 nm), for example. The inert gas may be nitrogen or argon gas though not limited thereto. The dose of UV radiation may be properly determined since the resulting chloro-terminated polysilane has a molecular weight which depends on the UV dose.

After exposure to a predetermined dose of UV, the reaction solution is concentrated to ½ to 1/5 in volume. Hexane is added to the concentrate such that about 150 grams of hexane is available per 10 grams of the polysilane, thereby causing the chloro-terminated polysilane (Mn≧1,000) to precipitate. Through filtration and drying, the end chloro-terminated polysilane is obtained as white powder.

The thus obtained chloro-terminated polysilane according to the present invention has reactive chlorine at both ends thereof and therefore, hydroxyl groups can be introduced at the both ends by hydrolysis or any other suitable technique. The resulting hydroxy-terminated polysilane may, in turn, be copolymerized with other polymers to form copolymers such as dialkylhydroxy-terminated polysilanes and dialkylvinylsiloxy-terminated polysilanes. In this regard, the chloro-terminated polysilane of the invention is a useful source material for forming copolymers with other polymers.

EXAMPLE

Examples of the present invention are given below by way of illustration and not by way of limitation. All percents are by weight. Mn and Mw are number and weight average molecular weights, respectively.

Examples 1-5

Methylphenylpolysilane having Mn=24,000 and Mw/Mn=3.32 was previously prepared by coupling reaction of methylphenyldichlorosilane with sodium. 7.0 grams of methylphenylpolysilane was dissolved in 133 grams of carbon tetrachloride. The solution had a concentration of 5%. In a nitrogen gas atmosphere, a Pyrex reaction tube with a diameter of 15 Mm was filled with the polysilane solution, closed with a plug, and exposed to UV radiation (312 nm) in a dose of 1 J/cm² using a high-pressure mercury lamp. The reaction solution was concentrated to about 50 grams. Addition of 100 grams of hexane to the solution caused precipitation of a chloro-terminated polysilane of the following formula (3). It was isolated by filtration and dried, obtaining a white powder (Example 1).

$$Cl-(CH_3C_6H_5Si)_p-Cl \qquad (3)$$

The procedure of Example 1 was repeated except that the UV dose was changed to 2, 3, 5 and 10 J/cm², yielding white powders (Examples 2-5).

Table 1 reports the Mn, Mw/Mn and yields of these white powders. Their chlorine contents as measured by titration are also reported together with the theoretical values.

TABLE 1

| | | Chloro-terminated polysilane | | | | |
|---|---|---|---|---|---|---|
| Example | UV dose (J/cm²) | Mn | Mw/Mn | Yield (%) | Cl (%) Found | Cl (%) Calc. |
| 1 | 1 | 15,970 | 2.34 | 77 | 0.45 | 0.45 |
| 2 | 2 | 12,220 | 1.94 | 65 | 0.54 | 0.58 |
| 3 | 3 | 11,980 | 1.93 | 63 | 0.58 | 0.59 |
| 4 | 5 | 8,300 | 1.70 | 60 | 0.84 | 0.86 |
| 5 | 10 | 4,600 | 1.47 | 52 | 1.49 | 1.53 |

Example 6

Methylphenylpolysiloxane having Mn=15,900 and Mw/Mn=10 was previously prepared by coupling reaction of methylphenyldichlorosilane with sodium. 0.5 grams of methylphenylpolysilane was dissolved in 9.5 grams of dichloromethane. The solution had a concentration of 5%. In a nitrogen gas atmosphere, a Pyrex reaction tube with a diameter of 15 Mm was filled with the polysilane solution,, closed with a plug, and exposed to UV radiation (312 nm) in a dose of 0.5 J/cm² using a high-pressure mercury lamp. The reaction solution was concentrated to about 2 grams. Addition of 20 grams of hexane to the solution caused precipitation of the product. It was isolated by filtration and dried, obtaining a chloro-terminated polysilane as a white powder.

Example 7

The procedure of Example 6 was repeated except that the UV dose was changed to 1 J/cm², yielding a white powder.

Example 8

Methylphenylpolysilane having Mn=15,900 and Mw/Mn=10 was previously prepared by coupling reaction of methylphenyldichlorosilane with sodium. 0.5 grams of methylphenylpolysilane was dissolved in 9.5 grams of 1,2-dichloroethane. The solution had a concentration of 5%. In a nitrogen gas atmosphere, a Pyrex reaction tube with a diameter of 15 Mm was filled with the polysilane solution, closed with a plug, and exposed to UV radiation (312 nm) in a dose of 0.5 J/cm2 using a high-pressure mercury lamp. The reaction solution was concentrated to about 2 grams. Addition of 20 grams of hexane to the solution caused precipitation of the product. It was isolated by filtration and dried, obtaining a chloro-terminated polysilane as a white powder.

Example 9

The procedure of Example 8 was repeated except that the UV dose was changed to 1.5 J/cm2², yielding a white powder.

Examples 10-12

The procedure of Example 6 was repeated except that the solvent was changed to chloroform, 1,1,2- trichloroethane and 1,1,2,2-tetrachloroethane, yielding chloro-terminated polysilanes as white powders (Examples 2-5).

Table 2 reports the Mn, Mw/Mn and yields of these white powders. Their chlorine contents as measured by titration are also reported together with the theoretical values.

TABLE 2

| Example | Methylphenyldi-chlorosilane (g) | Solvent Type | Amount (g) | UV dose (J/cm²) | Chloro-terminated polysilane Mn* | Mw/Mn | Cl content (ppm) Found | Cl content (ppm) Calc. | Yield (%) |
|---|---|---|---|---|---|---|---|---|---|
| 6 | 0.5 | dichloromethane | 9.5 | 0.5 | 13500 | 4.94 | 4900 | 5260 | 82 |
| 7 | 0.5 | dichloromethane | 9.5 | 1.0 | 10800 | 3.59 | 6200 | 6570 | 74 |
| 8 | 0.5 | 1,2-dichloroethane | 9.5 | 0.5 | 15000 | 7.00 | 4300 | 4730 | 76 |
| 9 | 0.5 | 1,2-dichloroethane | 9.5 | 1.5 | 11500 | 6.05 | 5500 | 6170 | 64 |
| 10 | 0.5 | chloroform | 9.5 | 0.5 | 13300 | 4.51 | 5000 | 5340 | 71 |
| 11 | 0.5 | 1,1,2-trichloroethane | 9.5 | 0.5 | 13000 | 5.20 | 5100 | 5460 | 65 |
| 12 | 0.5 | 1,1,2,2-tetrachloroethane | 9.5 | 0.5 | 12100 | 4.82 | 5300 | 5870 | 74 |

*calculated as polystyrene

Next, exemplary synthesis of a hydroxy-terminated polysilane from a chloro-terminated polysilane according to the present invention is described.

Reference Example 1

In 100 grams of THF was dissolved 5.0 grams of a chloro-terminated methylphenylpolysilane (Mn=7,500, Mw/Mn=1.57). To the solution, 0.2 grams of triethylamine was added, 3 grams of water was added dropwise, and the mixture was agitated under reflux for 4 hours. At the end of reaction, 100 grams of toluene was added to the reaction solution, which was washed with 100 grams of water three times. The organic layer was dried overnight over calcium chloride. After the desiccant was filtered off, the organic layer was concentrated, obtaining 3.5 grams of a white powder.

The results of analysis of this white powder are shown below which indicate that it is a both end hydroxy-terminated methylphenylpolysilane.

| | |
|---|---|
| Yield: | about 75% |
| Mn: | 7,550 (calculated as polystyrene) |
| Mw/Mn: | 1.64 |
| IR analysis: | peak at 3624 cm⁻¹ (Si—OH) |
| OH quantity: | 0.0260 mol/100 g (calculated: 0.0265 mol/100 g) |

Reference Example 2

In 300 grams of THF was dissolved 15.0 grams of a chloro-terminated methylphenylpolysilane (Mn=5,600, Mw/Mn=1.66). To the solution, 1.2 grams of triethylamine was added, 10 grams of water was added dropwise, and the mixture was agitated under reflux for 4 hours. At the end of reaction, 300 grams of toluene was added to the reaction solution, which was washed with 300 grams of water three times. The organic layer was dried overnight over calcium chloride. After the desiccant was filtered off, the organic layer was concentrated, obtaining 11.3 grams of a white powder.

The results of analysis of this white powder are shown below which indicate that it is a hydroxy-terminated methylphenylpolysilane.

| | |
|---|---|
| Yield: | about 75% |
| Mn: | 5,620 (calculated as polystyrene) |
| Mw/Mn: | 2.09 |
| IR analysis: | peak at 3624 cm⁻¹ (Si—OH) |
| OH quantity: | 0.0350 mol/100 g (calculated: 0.0356 mol/100 g) |

The process of the present invention facilitates synthesis of chloro-terminated polysilanes having a degree of polymerization of at least 5, especially at least 10. The chloro-terminated polysilanes allow various functional groups to be introduced therein and are useful source materials for forming copolymers with other polymers.

Although some preferred embodiments have been described, many modifications and variations may be made thereto in the light of the above teachings. It is therefore to be understood that within the scope of the appended claims, the invention may be practiced otherwise than as specifically described.

We claim:

1. A process for preparing a chloro-terminated polysilane comprising the step of exposing a chlorinated hydrocarbon solution of a high molecular weight polysilane to ultraviolet radiation in an inert gas atmosphere.

2. The process according to claim 1, wherein said chloro-terminated polysilane has the following formula $$Cl[(R^1R^2Si)_n(R^3R^4Si)_m]_kCl$$

wherein $R^1$, $R^2$, $R^3$ and $R^4$ are independently monovalent hydrocarbon groups having 1 to 12 carbon atoms and selected from substituted or unsubstituted alkyl and aryl groups, letters n, m and k are numbers in the range $0 \leq n \leq 10$, $0 \leq m \leq 10$, $n+m \geq 10$, and $k \geq 1$.

3. The process according to claim 1, wherein said high molecular weight polysilane has the following formula $$(R^1R^2Si)_{n'}(R^3R^4Si)_{m'}$$

wherein $R^1$, $R^2$, $R^3$ and $R^4$ are independently monovalent hydrocarbon groups having 1 to 12 carbon atoms and selected from substituted or unsubstituted alkyl and aryl groups, $0 \leq n'$, $0 \leq m'$, $n'+m' \geq 10$.

4. The process according to claim 3, wherein $n'+m' \geq 30$.

5. The process according to claim 3, wherein said high molecular weight polysilane has a number average molecular weight of from 1,000 to 1,000,000.

6. The process according to claim 3, wherein said high molecular weight polysilane has a number average molecular weight of from 5,000 to 1,000,000.

7. The process according to claim 1, wherein said chlorinated hydrocarbon is selected from the group consisting of dichloromethane, chloroform, carbon tetrachloride, 1,2-dichloroethane, 1,1,2-trichloroethane, and 1,1,2,2-tetrachloroethane and mixtures thereof.

8. The process according to claim 1, wherein said chlorinated hydrocarbon solution of a high molecular weight polysilane is from 1 to 20% by weight polysilane.

9. The process according to claim 1, wherein said chlorinated hydrocarbon solution of a high molecular weight polysilane is from 1 to 10% by weight polysilane.

10. The process according to claim 1, wherein said inert gas is nitrogen or argon.

* * * * *